United States Patent [19]

Nesathurai

[11] Patent Number: 4,983,307

[45] Date of Patent: Jan. 8, 1991

[54] METHOD FOR STERILIZING LIQUIDS BY ULTRAVIOLET RADIATION

[75] Inventor: Samuel A. Nesathurai, St. Clet, Canada

[73] Assignee: Serres Naturtek Greenhouses Inc., Les Cedres, Quebec, Canada

[21] Appl. No.: 388,502

[22] Filed: Aug. 2, 1989

[51] Int. Cl.$^5$ ............................................. C02F 1/32
[52] U.S. Cl. ..................................... 210/748; 422/24; 47/65
[58] Field of Search ............... 210/748, 764, 766, 900; 422/22, 24; 47/65

[56] References Cited

U.S. PATENT DOCUMENTS

| | | | |
|---|---|---|---|
| 2,189,279 | 2/1940 | Bitner | 210/748 |
| 4,179,616 | 12/1979 | Coviello et al. | 210/748 |
| 4,438,337 | 3/1984 | Forrat | 210/748 |
| 4,780,989 | 11/1988 | Mears et al. | 47/65 |

FOREIGN PATENT DOCUMENTS

| | | |
|---|---|---|
| 610989 | 7/1957 | Canada . |
| 674555 | 11/1963 | Canada . |
| 739145 | 7/1966 | Canada . |
| 767856 | 9/1967 | Canada . |
| 782201 | 4/1968 | Canada . |
| 790271 | 7/1968 | Canada . |
| 796014 | 10/1968 | Canada . |
| 841135 | 5/1970 | Canada . |
| 930924 | 7/1973 | Canada . |
| 934521 | 10/1973 | Canada . |
| 953871 | 9/1974 | Canada . |
| 966608 | 4/1975 | Canada . |
| 974024 | 9/1975 | Canada . |
| 999718 | 11/1976 | Canada . |
| 1048733 | 2/1979 | Canada . |
| 1054331 | 5/1979 | Canada . |
| 1062437 | 9/1979 | Canada . |
| 1072716 | 3/1980 | Canada . |
| 1081913 | 7/1980 | Canada . |
| 1089623 | 11/1980 | Canada . |

OTHER PUBLICATIONS

Buyanovsky, G., et al.; Ultra-Violet Radiation for the Inactivation of Microorganisms in Hydroponics; Plant and Soil (1981); 60: 131–126.

Ewart, J. M., et al.; Effects of Chlorine and Ultra-Violet Light in Disease Control in NFT; Acta Horticulturae (1980); 98: 317–323.

Howard, R. J.; Effecacy of the Trojan Ultraviolet Water Sterilizer for the Control of Plant Pathogens in Hydroponic Systems; A paper presented to the annual meeting of the Canadian Phytopathological Society; Jun. 20–23, 1982, at Edmonton, Alberta.

Fulton, H. R., et al.; The Fungicidal Action of Ultra-Violet Radiation; J of Agricultural Research (1929) vol. 38, No. 3.

(List continued on next page.)

Primary Examiner—Peter Hruskoci
Assistant Examiner—Krisanne Shideler
Attorney, Agent, or Firm—Foley & Lardner, Schwartz, Jeffery, Schwaab, Mack, Blumenthal & Evans

[57] ABSTRACT

A process and apparatus for reducing the dissemination of aquatic organisms and decreasing the risk of diseases caused by fungi, such as Pythium and Phythophthora spp, in greenhouse plants grown hydroponically by Nutrient Film Technique (NFT) by treating the water to be used in the NFT with ultraviolet radiation at a wave length of 2537 Å by passing the water in a zone of restricted width adjacent and exposed to the source of ultraviolet radiation and maintaining the temperature of the water in the range of 15° C. to 26° C. as it is passed at the zone. The apparatus includes an elongated cylindrical housing including a top cap and a bottom cap sealingly closing the cylindrical housing. A water inlet is located on the cylindrical housing near the bottom end cap and water outlet on the cylindrical housing near the top cap. An ultraviolet lamp in the form of an elongated cylindrical member extends concentrically within the housing and through the top cap and bottom cap. The top cap and bottom cap are removably secured to the cylindrical housing for access to the lamp and the interior of the housing.

1 Claim, 1 Drawing Sheet

OTHER PUBLICATIONS

Mone, J. G.; Ultra-Violet Water Purification; Pollution Engineering Magazine (1973); vol. 5, No. 12.

Price, T. V.; Control of Diseases in Hydroponic Systems; Government of Victoria, Agriculture Note Series No. 70 (1980).

Severin, B. F.; Disinfection of Municipal Wastewater Effluents with Ultraviolet Light;J. WPCF (1980); vol. 52, No. 7, pp. 2007–2018.

Severin, B. F.; et al.; Effects of Temperature on Ultraviolet Light Disinfection; Environ Sci. Technol. (1983); vol. 17, No. 12.

Yip, R. W., et al.; Ultraviolet Sterilization of Water—Its Potential and Limitations; Water and Pollution Control (1972).

Qualls, R. G., et al.; The Role of Suspended Particles in Ultraviolet Disinfection; Journal Water Pollution Control Federation (1983); vol. 55, No. 10.

METHOD FOR STERILIZING LIQUIDS BY ULTRAVIOLET RADIATION

BACKGROUND OF THE INVENTION

1. Field of the Invention

The present invention relates to an improved process and apparatus to reduce or eliminate species of fungi and algae from commercial greenhouse water using ultraviolet radiation.

2. Description of the Prior Art

Such fungi as *Pythium, Phythophthora,* and *Fusarium* spp in water seriously hamper the production of greenhouse vegetables grown hydroponically by the Nutrient Film Technique (NFT).

Nutrient Film culture is a viable soilless method for intensive crop production. The plants are grown in shallow channels containing a flowing nutrient solution which is continuously recirculated with some make up water added as the plants transpire. An NFT installation is a closed system with a volume of liquid maintained constant by a float valve which controls the supply of make up water and nutrient levels of the systems.

Advantages of the system include the efficient use of water and the elimination of expensive time-consuming processes associated with soil management.

One of the greatest dangers is that a disease causing organism will enter one channel and will be spread throughout the system by the recirculating solution and the whole crop will rapidly be wiped out. Pathogenes and pests may contaminate the system through water supplies. Growers are often faced with root rot, tobacco mosaic virus and wilt organisms, particularly *Fusarium, Pythium,* and *Verticillium* spp. Once systems are contaminated with pathogenes, the organisms are rapidly transmitted in the recirculating nutrient solution, causing severe crop injury and loss. The lack of pesticides registered in Canada for use in hydroponic systems makes control of pathogenes a persistent problem.

In addition to plant pathogens, algae growth is commonly seen in NFT systems. Algae may be found i coating holding tanks and troughs and may cause blockage in flow pipes and tubes. Once algae populations have become established, a great deal of hand labour is required to maintain effective levels of sanitation. Algae may also compete directly with the crop for oxygen and dissolved nutrients, thus requiring more frequent change of nutrient solution in the NFT system.

The primary mode of action in an ultraviolet fungicidal process is to damage the nucleus of the irradiated organism. The UV rays act to cleave nucleic acids resulting in damage to chromosomal components. This process is called lethal sectoring. Damaged cells that retain the ability to form clones are characterized by slow growth rates, increased radiosensitivity and a high degree of variability in the size and morphology of the cells and macro colonies. UV damage is also demonstrated by a partial loss of progeny in the next few generations.

The physiological process of inactivation, however, is not well understood and is complicated by the ability of many organisms to repair UV damage inflicted to their nucleic acid.

In spite of this, it is well known that exposure of microorganisms to UV light with wave length near 2537Å results in biochemical changes lethal to some organisms. The destruction of other bacteria, spores or viruses suspended in liquids very often gives survival curves of nearly logarithmic shape A 100% kill is rarely achieved.

Prior art fungicidal processes, used in England, include prophylactic substances which will prevent growth of disease causing organisms in the recirculating solution without adversely affecting crop production. Such substances are added to the solution and maintained at optimum concentration However, they present problems.

Adding the suggested 20 ppm of active etridiazole, as has been used in the United Kingdom, might be an example. Although such a concentration might possibly have no harmful effect on a tolerant crop, such as tomatoes, it might, under NFT conditions, have an adverse effect on more sensitive crops such as cucumbers. Etridiazole at a concentration of 20 ppm does not kill fungi; it merely inhibits their growth. It is, therefore, necessary to add etridiazole regularly because the substance does break down. There is mounting cost of application.

A different problem has been presented with an alternative prior art process. Aerial spray methods of disease control may be used in hydroponic greenhouses in England. These methods are similar to those applied to a conventional soil-grown crop. However, should some of the foliar spray enter the NFT channel, there is an undesirable effect of the solution around the roots.

In an NFT installation, the recirculating solution and the supply of make up solution can flow through a single pipe. It is convenient, therefore, to place in such a pipe, between the circulating pump and the inlet to the first NFT channel or in catchment tanks, an ultraviolet fungicidal unit. Because UV is a physical rather than chemical agent, it can be applied to an NFT system without producing toxic chemical residuals.

Preliminary trials suggest that the use of UV units affects the chelated iron in the solution Iron salts are essential nutrients in Nutrient Film culture Experimentation shows that some forms of chelated iron are more affected than others Mineral deposits out of the liquid form a coating on the surface of the UV lamp.

Prior art ultraviolet sterilizer units, such as manufactured by Trojan Environmental Products, are fitted with mechanical cleaners to remove precipitate from the bulb surface.

Another prior art sterilizer is described in Canadian Patent No. 1,062,437 by James H. Lewis. This disposable liquid sterilizer unit (comprising a jacket and tube) was clearly designed for house or cottage owners who require drinking water. The assembly also includes an activated carbon filter. The ABS jacket unit is factory sealed to the UV bulb and suffers from the disadvantage of reduced efficiency when the light source and jacket walls become coated with residue from water. In time, the unit must, therefore, be discarded.

Several forms of prior art commercially available UV sterilizers include an air space chamber between the UV bulb surface and the liquid envelope. Air drawn along the lamp can become ozone rich and brought in contact with cold untreated water. This process prevents precipitate build-up on the bulb. Many prior art commercially available UV sterilizers have been constructed with shielding devices to prevent cold water contacting the tube. Cold water on the surface of irradiated bulbs tends to decrease the life of underwater bulbs. Using cold contaminated water, with underwater UV bulbs, the kill rate drops. As disclosed in Canadian Patent No. 1,054,331, issued May 15, 1979, ultraviolet lamps operate at maximum efficiency on warm untreated water.

As the bulb becomes used and old, the voltage drop across the bulb changes. The wave length of light delivered also changes. Sterilizers currently available are fitted with complex switch devices, electrical current limiting resisters and light emitting diodes which indicate insufficient current to sterilize water.

SUMMARY OF THE INVENTION

The object of this invention is to provide an ultraviolet sterilization process in which nutrient-enriched water is satisfactorily cleared of fungi and microorganisms.

A further object of the present invention is an improved sterilization apparatus in the form of a robust compact repairable unit with an ultraviolet bulb properly positioned in the optimum location within the unit.

In a process in accordance with the present invention for reducing the dissemination of aquatic organisms and decreasing the risk of diseases caused by fungi, such as *Pythium* and *Phythophthora* spp, in greenhouse plants grown hydroponically by Nutrient Film Technique (NFT) by treating the water to be used in the NFT with ultraviolet radiation at a wave length of 2537Å by passing the water in a zone of restricted width adjacent and exposed to the source of ultraviolet radiation and maintaining the temperature of the water in the range of 15° C. to 26° C. as it is passed at the zone.

An apparatus according to the present invention comprises an ultraviolet unit including an elongated cylindrical housing to be mounted in a vertical attitude. The cylindrical housing includes, when in a vertical attitude, a top cap and a bottom cap sealingly closing the cylindrical housing at the top and bottom ends respectively. A water inlet is located on the cylindrical housing near the bottom end cap and water outlet on the cylindrical housing near the top cap. An ultraviolet lamp in the form of an elongated cylindrical member extends concentrically within the housing and through the top cap and bottom cap. The cylindrical housing and the cylindrical lamp member define an elongated narrow annular chamber extending at least between the water inlet and outlet ports. Means are provided for sealing the top cap and bottom cap to the cylindrical lamp member near each end respectively. The top cap and bottom cap are removably secured to the cylindrical housing for access to the lamp and the interior of the housing.

BRIEF DESCRIPTION OF THE DRAWINGS

Having thus generally described the nature of the invention, reference will now be made to the accompanying drawings, showing by way of illustration, a preferred embodiment thereof, and in which.

DESCRIPTION OF THE PREFERRED EMBODIMENTS

Figures 1, 2, 3:
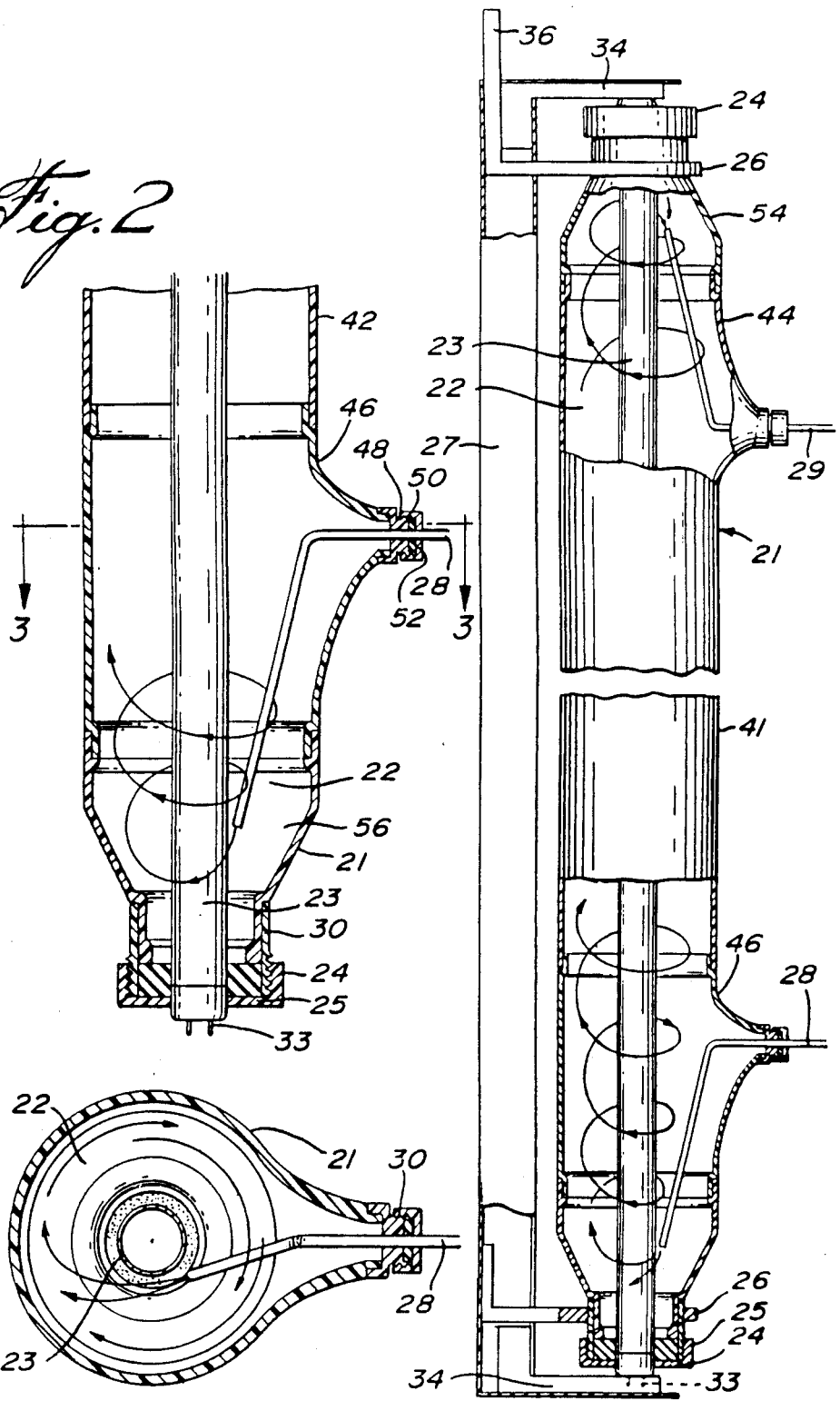
FIG. 1 is an axial cross-section of an irradiation unit in accordance with the present invention.
FIG. 2 is a fragmentary enlarged elevation view, partly in cross-section, of a detail shown in FIG. 1.
FIG. 3 is a horizontal cross-section, taken along line 3—3 of FIG. 2.

Referring now to the drawings, the ultraviolet sterilization apparatus is shown as having an elongated circular cylindrical housing 21 defining an untreated water chamber 22 surrounding an elongated ultraviolet bulb 23. The housing 21 is fabricated of black ABS (acrylonitrile butadiene styrene). An ABS plumbing pipe was chosen primarily because of availability in hardware outlets across North America. The ABS jacket is UV resistant. ABS stabilization has prevented the UV induced polymer from deteriorating and discoloring. Another quality of ABS is thermal insulation. Preheated water fed to the apparatus does not rapidly lose heat. Typical applications of ABS include plumbing components and conduits ABS pipe assemblies include snap fits, threaded screws and adhesive bonding in the form of uniformly dispersed polymer mixed with rubber latex which is easy to handle. ABS pipes and accessories can be cut with a hand saw to any length or be bought in injection molded and extruded form. It is a resin approved by National Sanitary Foundation for use in portable water installations. The ABS components are adhesive bonded together to form a durable one-piece housing 21. ABS injection molded parts include threaded screw nipples which can be fitted with polyethylene washers and ABS end caps. These replaceable washers fit tightly against the UV bulb surface preventing moisture from leaking out of the jacket.

In the construction of the apparatus, it is important to choose a material which is nonphytotoxic. Materials have been chosen which have no detrimental effect on the plants. Phytotoxicity has not been reported with the use of ABS material. Furthermore, ABS material does not rust or produce contaminants into the water in the apparatus. The ABS fabricated housing 21 is black and opaque to UV radiation of any wave length which may injure the skin or eyes of any person who is near the apparatus.

The housing 21 includes, therefore, a straight pipe section 41 joined at the top and bottom ends thereof to tee fittings 44 and 46. Each tee fitting includes a threaded nipple 48 adapted to receive a flange nut 50 which in turn seals an annular gasket 52 against the end surface of the nipple 48. An inlet conduit 28 extends through the gasket 52 and into the housing 21 as will be described later. The gasket 52 is preferably made of polyethylene material. The conduit 28, for instance, will be solvent welded to the gasket 52 to provide a water sealed assembly. The fitting 44 is of identical construction to the fitting 46, and the connection of the inlet conduit 28 to this fitting is identical to the outlet conduit 29 passing through the fitting 44.

At each end of the housing 21 there is provided a reducing fitting 54 and 56. The reducing fitting provides a neck at each end to which a threaded coupling 30 is solvent welded to the fitting 56, as shown in FIG. 2. Of course, both ends of the housing 21, that is, the fittings 54 and 56, are identical, and only the bottom fitting 56 will be described. A flange cap 24 is adapted to threadably engage the coupling 30 and to secure a gasket 25 against the end of the coupling 30. The gasket 25 has a central opening therein which will be matched to the outer diameter of the ultraviolet bulb 23. A solvent adhesive which can be applied to the surface of the ultraviolet bulb 23 and which will seal the gasket to the bulb is also provided. At each end of the ultraviolet bulb there is a pair of prongs for electrically connecting the bulb to a suitable socket 34. An electrical mounting bracket 27 having a pair of sockets 34 is provided for mounting the complete unit as shown in FIG. 1. Clamps 26 are mounted to the bracket 27 for retaining the housing 21 at each end thereof. A hanging strap 36 may be provided for supporting the assembly in a vertical attitude.

A person with no specialized skill can disengage the power source, loosen the screw caps 24 to wash the unit, assemble it and install it into its electrical fixture 27. The end caps 24 enable the apparatus to be dismantled, cleaned and assembled quickly and easily. This apparatus is designed to be assembled and be in complete operation within five minutes. The components can be washed frequently with household bleach, rinsed with tap water or replaced when necessary. Frequent washing prevents the accumulation of impurities on the surface of the bulb 23. Such impurities are one of the main causes of the relatively short life of presently available water contacting UV sources.

A simple ABS housing 21 with a water intake 28 at the bottom of the vertically mounted apparatus is provided. The water tube 28 extends at an angle into the housing 21 so that the intake water is made to enter the housing 21 with turbulence. Strong turbulence created within a few inches of the intake pipe 28 can produce swirling of the untreated water around the surface of the ultraviolet bulb 23 as the water fills the capacity of the chamber 22. The untreated water is maintained in the configuration of a thin layer, initially spiraling over the surface of the bulb 23 continually, partially cleaning the glass-liquid interface.

Table 1 shows examples of two units with unit 1 having a greater diameter than unit 2. Tests have shown that the smaller diameter unit 2 has a greater potential to irradiate fungi and microorganisms.

TABLE 1

|  | Unit 1. | Unit 2. |
| --- | --- | --- |
| Inside diameter of ABS jacket (inches) | 3.000 | 2.000 |
| Outside diameter of UV bulb (inches) | 1.450 | 1.450 |
| Length of UV bulb (inches) | 48.000 | 48.000 |
| Length of ABS jacket (inches) | 47.000 | 47.000 |
| Radius of annular (jacket-bulb) (inches) | 0.775 | 0.275 |
| Volume of water chamber (cu. inches) | 254.570 | 70.100 |
| Flow rate | 4 liters p.m. | 4 liters p.m. |

In operation, the apparatus is consistent, easy, safe and dependable. The apparatus has no need of complex sight ports since the bulb ends protrude out of the jacket enough for operation to be seen. Failure of the sterilization process, for any reason, breakage, burnout of the lamp or interruption of electrical power, can be seen. The operation can be easily stopped manually, preventing untreated water from being delivered from the apparatus.

However, to prevent the bulb from rendering ineffective sterilization radiation when it only appears to be functional, it can be checked with a voltmeter before assembly, thus eliminating the need for electrical switch mechanisms within the design procedures. Furthermore, since the radiation wave length does decrease with time, such an easy to handle apparatus does not require replacing the whole cartridge, or removing cleaning equipment, scrapers, and turbulence creating discs.

With this simple single lamp construction, hundreds of gallons of untreated water are processed, thus substantially reducing operating costs. The improved apparatus provides intimate contact of the warm untreated water with the radiating source as required in order to effect sufficient sterilization. Moreover, the water remains in the area of intense radiation long enough to ensure that adequate sterilization is effected. The inventor has found that decreasing the water speed increases the fungicidal action. Spreading the fluid into a laminar flow attitude in such close proximity to the irradiating source rapidly reduces the source of disease in plants grown hydroponically.

*Pythium* spp actively regenerates in warm water. Ultraviolet rays are more effective as a fungicide when used on fungi as they are procreating. This process permits an ultraviolet bulb to operate at its most effective temperature.

Untreated water is preheated to 15° to 26° C. The warm untreated water comes in contact with and is irradiated by the UV bulb. The warm untreated water outside the bulb surface maintains UV bulb optimum firing temperature inside the bulb so that the bulb continually generates radiation of wave length 2537A. Heat generated by the UV bulb raises the temperature of the untreated water to a temperature which is satisfactory for plant root growth in the Nutrient Film culture. Warm untreated water becomes saturated with massive doses of ultraviolet radiation causing maximum reduction in number/unit fluid volume of live or active bacteria, fungi or other microorganisms in the water. Using untreated, preheated water in intimate contact with the bulb surface, the practical efficiency life of the ultraviolet source is considerably increased.

It is known that there are two types of *Pythium* which can destroy tomatoes when grown in a hydroponic culture. These are *Pythium aphanidermatum* and *Pythium ultimum*. These two organisms were found to alternate in predominance as the causal agent of root rot in tomatoes. One of the reasons for the occurrence of these two species appeared to be related to the temperature of the incoming well water and the circulating nutrient solution. During the summer season, or when solution temperatures ranged from 22° to 28° C., *Pythium aphanidermatum* is the predominant species. This species is adapted to warm temperatures since it has mobile spores and will irradicate tomatoes at about 28° C. The operating temperature of an NFT catchment tank should be maintained between 18° and 26° C.

In supply tanks where temperatures range from 10° to 23° C., Pythium ultimum was the predominant species. This species is adapted to cool temperatures, has no mobile spores, and can irradicate tomatoes at a temperature less than 20° C.

An ultraviolet radiation apparatus as described above can be set up at the make up water inlet for a supply tank for a greenhouse where the water is made up from the well and thus in the colder temperature ranges. Accordingly, the ultraviolet rays would act to cleave the nucleic acids, resulting in damage to chromosomal components of the *Pythium ultimum* as it enters the supply tank. A supply tank of this type would be maintained by either heating in winter or cooling in summer to between 18° and 20° C.

It has been found that *Pythium aphanidermatum*, on the other hand, will procreate in the temperature range of 18° to 23° C. Warm contaminated water at about 23° C. is thus pumped from the supply tank through an ultraviolet radiation unit of the type described, and it has been found that maximum fungal damage is achieved at these warmer temperatures.

The efficiency of the sterilization process may be affected not only by temperature of the untreated liquid and firing temperature of the UV ray generation tube, but also by the film thickness of the untreated water, proximity of the liquid to the source of ultraviolet rays, liquid speed in the apparatus and the cleanliness of the apparatus from precipitate.

The diameter of the envelope around the UV bulb is chosen so that every microorganism in untreated water in the envelope is effectively irradiated. The envelope length is chosen to fit the total effective UV bulb length.

The ultraviolet sterilization unit provides for a thin film of preheated water completely surrounding and in contact with the full length of the cylindrical 48 inch ultraviolet bulb. The elongated sterilization chamber is a narrow radial envelope surrounding the maximum surface area of the bulb. The water can be preheated to 15° C. to 26° C. to first satisfy the plant root temperature and, secondly, to increase the UV bulb efficiency. The continuous stream of untreated water flows over the bulb at a maximum rate of 4 liters per minute. Because of this low volume laminar flow, the bulb subjects the total fluid to ultraviolet rays of the required intensity and successfully reduces the number of microorganisms in the water.

Recent attention has been given to the disadvantages of using chemical fungicides. Ultraviolet radiation is a physical change of untreated water. Irradiation produces no change in pH, important chemical structure or flavour of the Nutrient Film culture. Furthermore, some changes in chelated iron have some advantages in the system.

I claim:

1. A process for reducing the dissemination of aquatic organisms and decreasing the risk of diseases caused by fungi of *Pythium* and *Phythophthora* spp in greenhouse plants grown hydroponically by Nutrient Film Technique (NFT), consisting essentially of treating the water to be used in the NFT with ultraviolet radiation at a wavelength of 2537Å by passing the water in a zone of laminar flow in contact with and exposed to the surface of an ultraviolet radiation source and maintaining the water in the range of 18° to 23° C. as it is passed in the zone.

* * * * *